United States Patent

Lindsey et al.

[11] Patent Number: 5,807,322
[45] Date of Patent: Sep. 15, 1998

[54] PUMPING AND PRESSURE DETECTION USING FLEXIBLE TUBES

[75] Inventors: Michael J. Lindsey, Berkhampsted; David R. Coulson, Watford, both of United Kingdom

[73] Assignee: Graseby Medical Limited, Hertfordshire, United Kingdom

[21] Appl. No.: 716,152

[22] PCT Filed: Mar. 21, 1995

[86] PCT No.: PCT/GB95/00619

§ 371 Date: Sep. 12, 1996

§ 102(e) Date: Sep. 12, 1996

[87] PCT Pub. No.: WO95/25893

PCT Pub. Date: Sep. 28, 1995

[30] Foreign Application Priority Data

Mar. 21, 1994 [GB] United Kingdom ................... 9405523

[51] Int. Cl.⁶ .................................................. A61M 31/00
[52] U.S. Cl. ............................................................ 604/65
[58] Field of Search ................................. 604/30, 31, 49, 604/50, 65–67, 118; 128/DIG. 12, DIG. 13

[56] References Cited

U.S. PATENT DOCUMENTS

| | | | |
|---|---|---|---|
| 4,239,464 | 12/1980 | Hein | 417/474 |
| 4,255,088 | 3/1981 | Newton et al. | 417/1 |
| 4,277,226 | 7/1981 | Archibald | 417/38 |
| 4,617,014 | 10/1986 | Cannon et al. | 604/67 |
| 4,650,469 | 3/1987 | Berg et al. | 604/131 |
| 4,690,673 | 9/1987 | Bloomquist | 604/67 |
| 5,103,211 | 4/1992 | Daoud et al. | 340/608 |
| 5,292,306 | 3/1994 | Wynkoop et al. | 604/51 |

FOREIGN PATENT DOCUMENTS

| | | |
|---|---|---|
| 0182502 | 5/1986 | European Pat. Off. . |
| 0225158 | 6/1987 | European Pat. Off. . |
| 0429866 | 10/1990 | European Pat. Off. . |
| 0526962 | 3/1992 | European Pat. Off. . |
| 3803594 | 8/1989 | Germany . |

*Primary Examiner*—Michael Buiz
*Assistant Examiner*—Manuel Mandez
*Attorney, Agent, or Firm*—Price, Heneveld, Cooper, DeWitt & Litton

[57] ABSTRACT

A peristaltic pump unit (18) has a flexible infusate line (28) which is repeatedly compressed by a flat plate like pusher (30). Transverse valve plates (32, 34), on either side of the pusher (30), operate sequentially to close the line in front of and behind the pusher. A resistive pressure sensor (50), between the two valves, provides signals to a microprocessor (46) which provides the system monitoring capabilities. Consistency in dose rate is provided by arranging for the flexible line (28) to be received in an elongate groove or channel (58) which acts to restrain sideways bulging of the line as it is being compressed by the pusher.

29 Claims, 10 Drawing Sheets

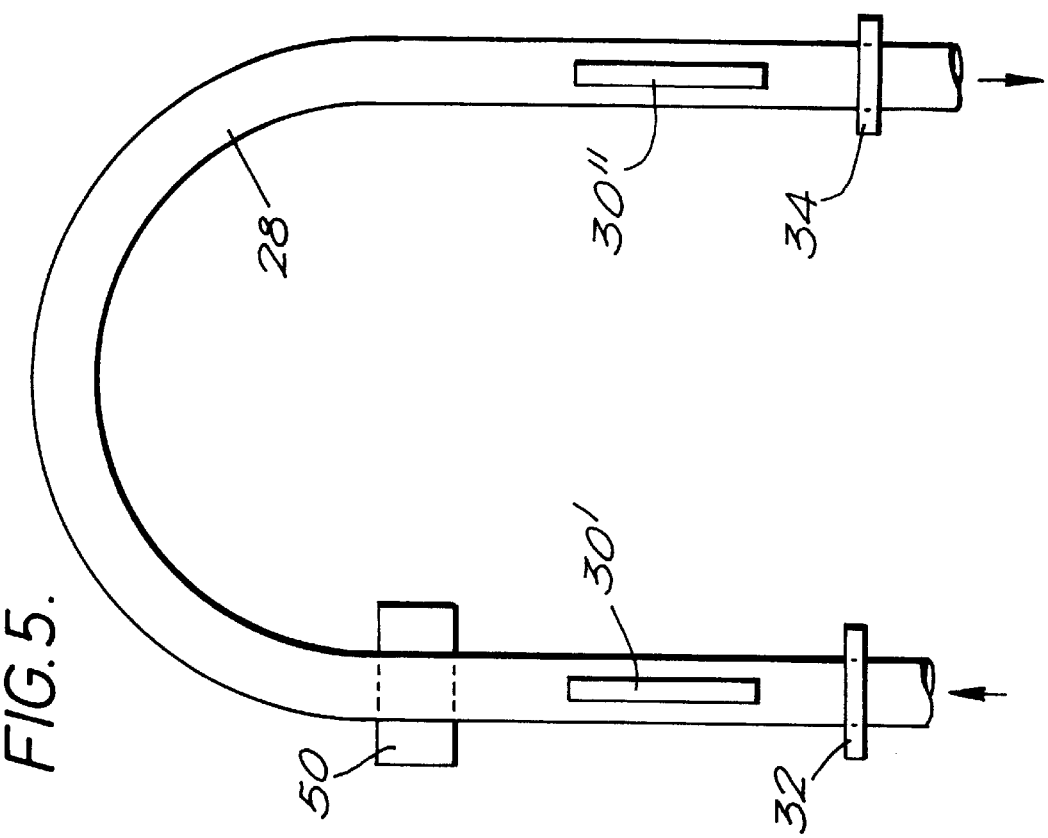
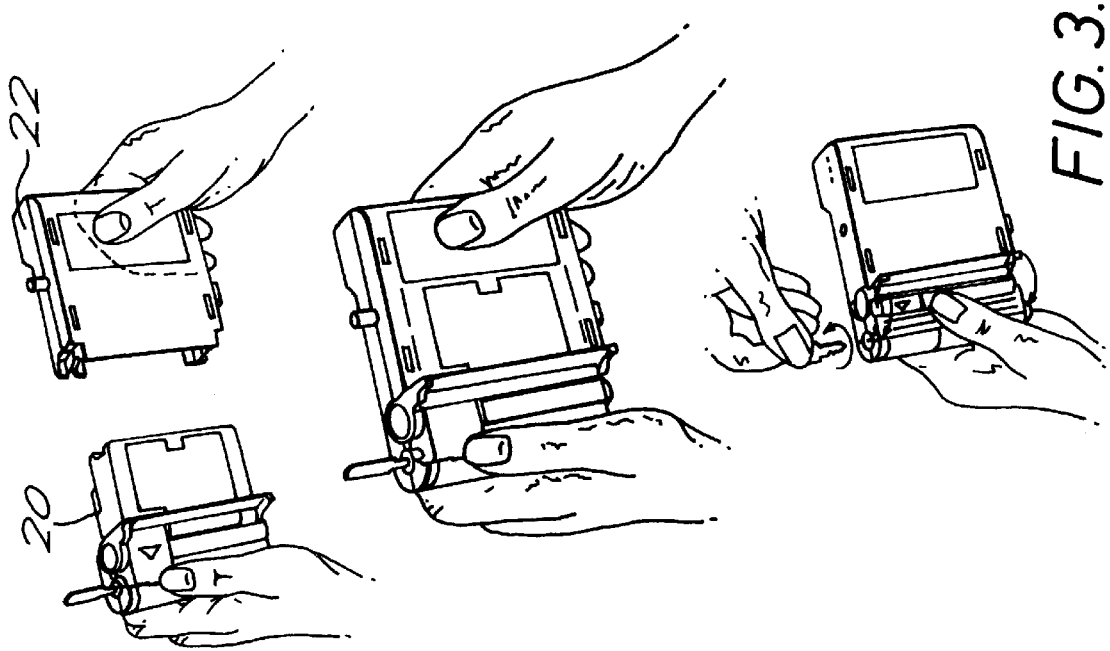

PUMPING AND PRESSURE DETECTION USING FLEXIBLE TUBES

The present invention relates to peristaltic pumps, and in particular although not exclusively to peristaltic pumps for portable drug infusion devices. In certain aspects, the invention further relates to pressure detecting within flexible tubes generally.

A peristaltic pump comprises a length of flexible tubing along which a fluid is to be moved. There are various types of peristaltic pump, but in one type the pumping pressure is provided by an external pusher or piston which partially compresses the tube, the liquid being constrained to move in one direction only by some sort of non-return valve arrangement such as movable fingers which act to compress and seal the tube. This is known as a three-finger pump. In another type of pump—the linear peristaltic pump—a plurality of fingers move up and down, each finger compressing the tube at a different point. A camshaft mechanism ensures that the fingers move in a wave-motion-like sequence that forces fluid through the tube. In yet another type—the rotary peristaltic pump—the tube is carried in a circular track, and fluid is pushed along using one or more rollers.

Peristaltic pumps have been used for some time in devices for continuous drug infusion, and they are particularly convenient, because of their simplicity and small size, for use in portable devices for delivering continuous relatively large doses of drugs (for example anti-cancer drugs) to ambulatory patients.

Problems with such devices in the past have included the difficulty of providing, conveniently and cheaply, a reliable pump monitoring mechanism which can rapidly warn the patient if anything goes wrong with the infusion. The three-finger pump (which is otherwise very suitable for use in drug infusion devices) is rather non-linear, in that the fluid displacement is a non-linear function of the amount by which the tube is compressed. FIG. 1 shows, schematically, the plunger finger 12 of a conventional prior art three-finger peristaltic pump, in which a tube 10 is compressed between a pusher or plunger, which moves downwardly in the direction of the arrow 14, and a stationary pressure plate 16. It will be appreciated that the plunger 12 may also move upwardly against the direction of the arrow 14 to reduce compression of the tube. It will be seen that as both the plunger and the pressure plate are flat and parallel, with both being much wider than the tube, the tube as it is compressed bulges out sideways into the oval shape shown.

If the distance d is taken to be the minimum distance between the plunger 12 and the pressure plate 16, it is found in practice that the fluid displacement of the pump is a non-linear function of d. The force that is needed to move the plunger downwardly is also a non-linear function of d. In a conventional infusion pump, used for the infusion of drugs, either or both of the tube 10 and the pressure plate 16 are likely to be replaceable. Accordingly, if accurately repeatable infusion rates are to be achieved, it is essential that the replaceable tube and/or back plate can be positioned very accurately with respect to the plunger 12. If the size or thickness of the replaceable tube differs, or if the pressure plate 16 is not mounted in exactly the same position as it was previously, the infusion rate is likely to differ.

It is an object of the present invention to provide a peristaltic pump in which at least some of the above difficulties are at least ameliorated.

It is a further more general object to provide a peristaltic pump which incorporates an improved mechanism for pump monitoring.

According to a first aspect of the present invention there is provided a peristaltic pump comprising a flexible line carrying fluid to be pumped, cyclical line compression means arranged repeatedly to compress the line, pressure sensing means arranged during part of the cycle to provide a signal representative of a downstream pressure, and during another part of the cycle to provide a signal representative of an upstream pressure, the said signals being supplied to pump monitoring means, and the monitoring means having indicator means arranged to provide a pump status indication.

According to a second aspect of the present invention there is provided a peristaltic pump comprising a flexible line carrying fluid to be pumped, line compression means arranged repeatedly to compress the line, an input valve upstream of the line compression means and an output valve downstream of the line compression means, pressure sensing means arranged to provide a signal representative of the pressure in the line between the input and output valves to a pump monitoring means, the monitoring means having indicator means arranged to provide a pump status indication.

According to a third aspect of the invention there is provided a peristaltic pump including a flexible line carrying fluid to be pumped, line compression means arranged repeatedly to compress the line, an input valve upstream of the line compression means and an output valve downstream of the line compression means; the line compression means comprising a member which is arranged to compress the line against a support, the pump including restraining means preventing or restraining the line from bulging in a direction perpendicular to the compression direction.

The invention extends to a drug infusion unit incorporating a peristaltic pump as previously defined.

The invention further extends to devices using flexible tubes, which are not necessarily pumps. For example, according to yet a further aspect of the invention there is provided a contamination-in-line detector which comprises a line through which in use a fluid flows, pressure means arranged to apply pressure to the fluid within the line between an input valve and an output valve, and pressure sensing means arranged to provide a signal representative of the pressure in the line between the input and output valves when both the valves are closed and pressure is being applied by the pressure means.

The pressure sensing means may also be arranged to provide a signal representative of the pressure in the line when either or both of the valves are open, and/or when both of the valves are closed but no pressure is being applied by the pressure means. Comparison means may be provided to compare the two pressures, and thereby a determination of whether there is contamination in the line. Calculation means may also be provided to produce an estimate of the amount of contamination.

The peristaltic pump may be associated with a cassette which acts as a reservoir for the fluid to be pumped. In a preferred embodiment, the pump may incorporate a "cassette empty" alarm and a "cassette removed" alarm.

In the preferred embodiment, the line is flexible and the pressure means acts by compressing the line, thereby applying pressure to the fluid within the line.

In the preferred embodiment, the fluid flowing through the line is a liquid (for example an infusate), and the detector is arranged to detect the presence of air or any other gas within the line. The air or gas may be a contamination in the form of large air bubbles, or the air or gas may be incorporated within the fluid itself, making up a foam. In either case, the difference in compressibility with air or gas present and without air or gas present enables one to determine the extent of the contamination.

It would also be possible for the same principles to be used if the fluid flowing along the tube were to be an air or gas, and the contamination a liquid or foam.

The invention set out above is, more generally, capable of providing an estimate of the amount of air or other gas in the line, compared with the amount of liquid. If it is intended that both gas and liquid should be passing along the line (for example if the line is intended to carry a foam), the invention may be used to estimate the ratio of gas to liquid (for example the density of the foam). Of course, with such an arrangement the device is not detecting contamination, but merely the proportions of two difference substances, both of which are intended to be there. With such a perspective, the invention may be generally characterised as being an air-in-line detector or a liquid-in-line detector. It is of course possible, although not essential, that such a detector could be used within a peristaltic pump.

According to a further aspect of the invention there is provided a gas-in-line detector which comprises a line through which in use a fluid flows, pressure means arranged to apply pressure to the fluid within the line, pressure sensing means arranged to provide a signal representative of the pressure in the line, and converter means adapted to convert the signal into a value representative of a level of gas in the line or to provide an indication of the magnitude of the signal relative to a predetermined value. The converter means may indicate whether the signal is larger than the predetermined value.

In one embodiment, the input and output valves, mentioned above, may be replaced by permanent closures. For example, an air-in-line detector may comprise a flexible tube section closed off at both ends and compressed, the rise in pressure during the compression being related to the gas/liquid proportions within that section. The greater the proportion of gas, the less the pressure increase.

Instead of applying pressure to the fluid within the tube by compressing a flexible line, other methods of applying pressure could be envisaged. For example, one might instead use a generally rigid tube, the fluid inside the tube being hydraulically or pneumatically connected to a movable piston. A pressure increase can then be applied, manually or automatically, by pushing in the piston.

Monitoring the pumphead by positioning the pressure sensor adjacent to the expulsor (or pusher) is a very convenient and inexpensive method that has many advantages: one can make do with an inexpensive sensor, and with minimal electronic hardware; very little space is taken up; air in the line can be detected with clear, opaque and fatty infusates; air bubbles can be detected, thus reducing shot-size inaccuracies; the downstream occlusion pressure may be set by software to any level within the working range; shot size errors due to downstream pressure variations may be compensated for; and the upstream pressure can be measured.

The invention further extends to any individual feature or compatible combination of features mentioned above or elsewhere in the patent application. In particular, features from any aspect mentioned above, and the corresponding claims set out at the end, may be combined with features from any other aspect, and its corresponding dependent claims. In addition, features referred to as relating to the peristaltic pump aspects of the invention may also be applicable to the drug infuser aspects, and vice-versa. Either may be combined, more generally, with any one or more of the features relating to the contamination-in-line detector, the air-in-line or the liquid-in-line detector.

The present invention may be carried into practice in a number of ways and preferred specific embodiments will now be described, by way of example, with reference to the accompanying drawings, in which:

FIG. 3 illustrates insertion and removal of the disposable cassette into the unit of FIG. 2;

FIG. 5 shows one preferred embodiment for the arrangement of the tube, the pushers and the valves;

Figure 1:
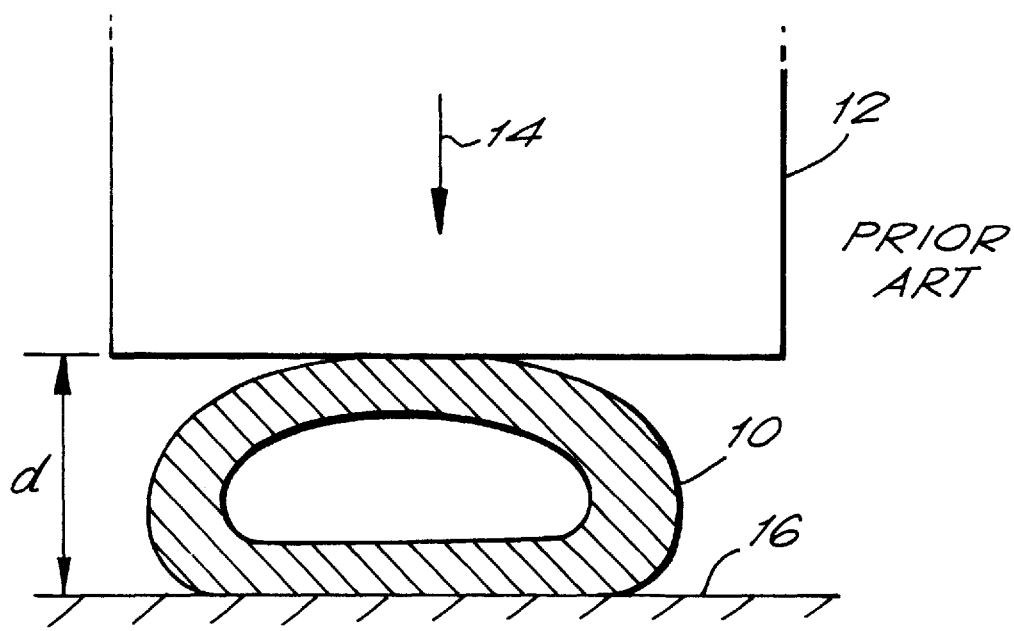
FIG. 1 shows a cross-section of part of a conventional peristaltic pump, already described.
Figure 2:
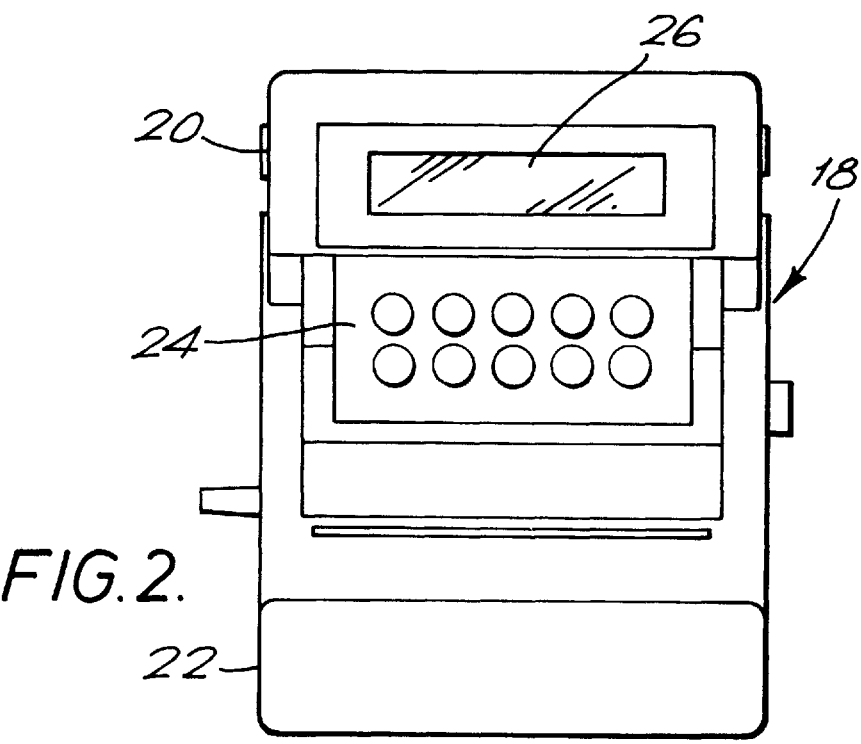
FIG. 2 shows a drug infusion unit, incorporating a pump embodying the present invention.

The infusion pump unit 18 shown in FIG. 2 is designed to deliver drugs to ambulatory patients. The unit comprises a main body 20 to which is releasably attached a cassette 22 (sometimes known as a "disposable"), inside which there is a flexible bag (not shown) containing the infusate. The unit is controlled by means of buttons on a program card 24, and there is also an LED display 26 which indicates to the patient or physician the status of the unit. The unit also has an audible alarm.

FIG. 3 shows how the replaceable cassette 22 is secured to the main body 20 of the unit. The details of the specific attachment mechanism are not of particular importance to this patent.

Figure 4:
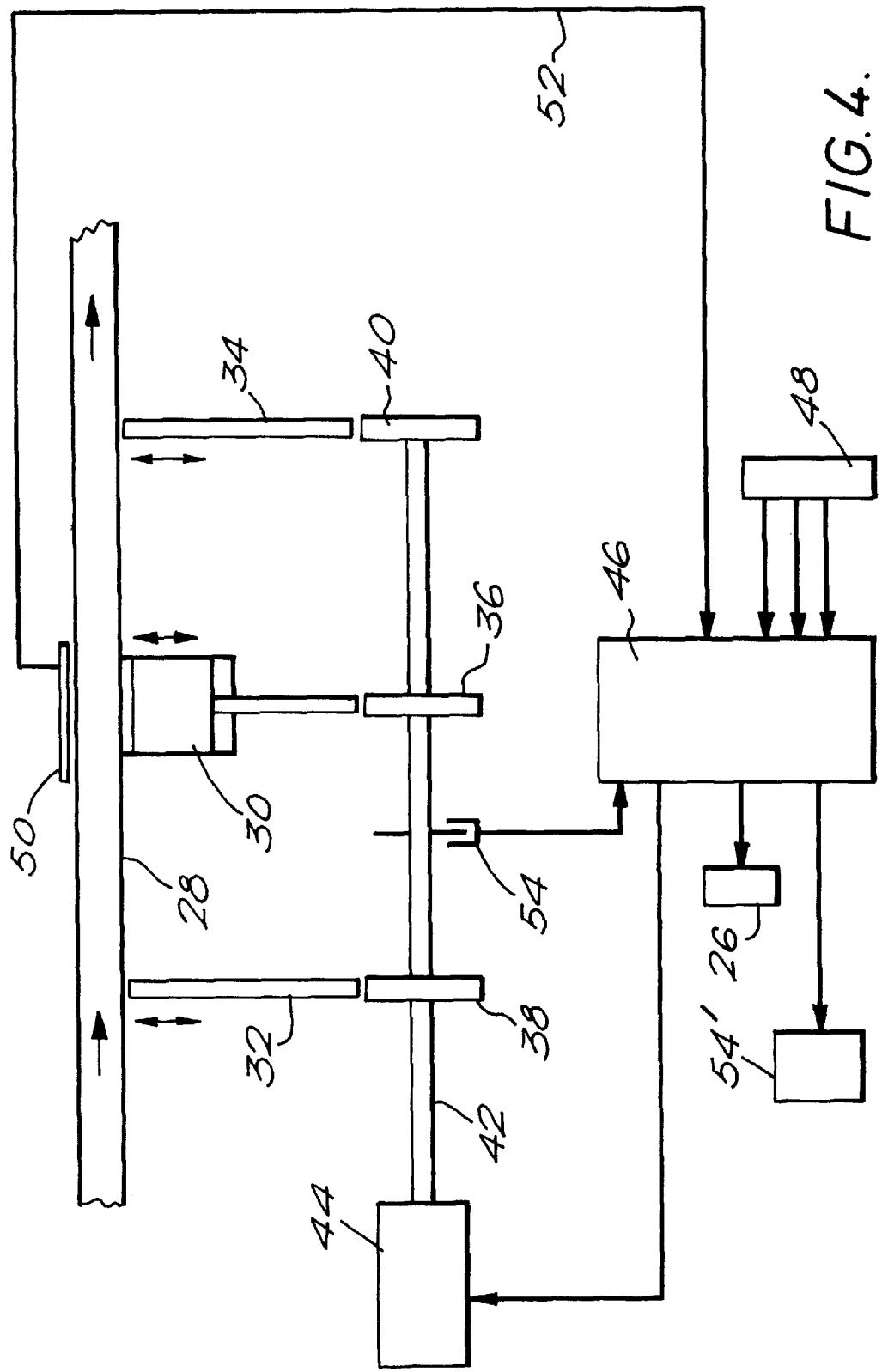
FIG. 4 is a schematic diagram illustrating the operation of the unit.

Within the replaceable cassette 22, the infusate is stored within a flexible sterilised bag (not shown) moulded to which is an infusion line, which the patient would attach to a cannula in the usual way. The main pumping mechanism, along with the unit electronics, are all contained within the main body 20. To enable the infusate to be delivered at a constant rate to the patient, the body 20 incorporates a miniature peristaltic pump. This is schematically shown in FIG. 4.

The pumping action actually operates on the flexible, replaceable infusion line 28 that extends between the infusate bag (not shown) and the cannula (not shown). Pumping pressure within the line 28 is obtained by means of a pumping piston or finger 30 which repeatedly presses upon and partially compresses the line 28 against a pressure plate (not shown in FIG. 4). To ensure that the infusate moves in the correct direction along the line 28, there are upstream and downstream valves 32,34 which repeatedly press down hard on the line, to seal it. When the valve 32 is closed, the piston 30 presses down on the line, and forces the infusate past the open valve 34. The valve 34 is then closed, and the valve 32 opened. When the piston 30 is retracted, the tube springs back into its normal shape, by virtue of its natural resiliency, and this draws liquid along from the bag past the now open valve 34. The valve 32 is then closed, the valve 34 opened, and the process repeated.

Synchronisation of the piston 30 and the valves 32,34 are provided by respective cams 36 and 38,40. It would also be possible to provide the synchronisation electronically rather than mechanically.

The cams are mounted to a shaft 42 of a motor 44, the operation of which is controlled by a microprocessor 46. According to the drug or other infusate to be supplied along the line 28, the motor 44 may either operate continuously, or it may operate intermittently, causing the pump to undergo one pumping cycle at the required intervals. The microprocessor 46 may have external user-controlling means 48, such as for example the program card 24 shown in FIG. 2.

The peristaltic pump shown in FIG. 4 incorporates a resistive pressure sensor 50 for pump monitoring purposes. The pressure sensor produces a signal which is representative of the pressure in the line between the two valves 32,34 and it passes that signal along an electrical line 52 to the microprocessor 46. The microprocessor is therefore able to monitor how the pressure in the line 28 varies throughout the pumping cycle. An opto-position sensor 54 provides the microprocessor with synchronisation signals so that it is always aware of the current phase within the pumping cycle. The preferred opto-position sensor makes use of a black and white segmented disk, but of course any other convenient position sensor could be used.

As will be described in more detail below, the microprocessor makes use of the signals from the pressure sensor 50 and the position sensor 54, to determine whether any fault conditions exist. If such a condition does exist, a message is displayed on the LCD screen 26, and an audible alarm 54 is actuated.

In this embodiment of the device, the line 28 is not actually straight in the region of the pump, as is shown in the schematic diagram of FIG. 4. FIG. 5 shows more clearly the actual arrangement, and it will be seen that the line 28 is actually looped to save space. The valves 32,34 are, as may better be seen in this view, flat plates which are positioned perpendicular to the line so that they can effectively squash it and seal it. The piston 30 actually comprises two separate elongate fingers 30',30" which both press down along the length of the line 28. The two fingers 30', 30" always press down together in synchronisation, whereas the valves 32,34 act alternately. The pressure sensor is positioned underneath a straight part of the tube, as that has been found in practice to provide more reliable and consistent results than having the sensor under a curved section of the tube. Although not shown in FIG. 5, the curved portion is actually out of the plane of the diagram, to allow a further reduction in device size without forcing the line 28 around too tight a bend. In an alternative embodiment, the line in FIG. 5 could be straight rather than curved.

Figure 6:
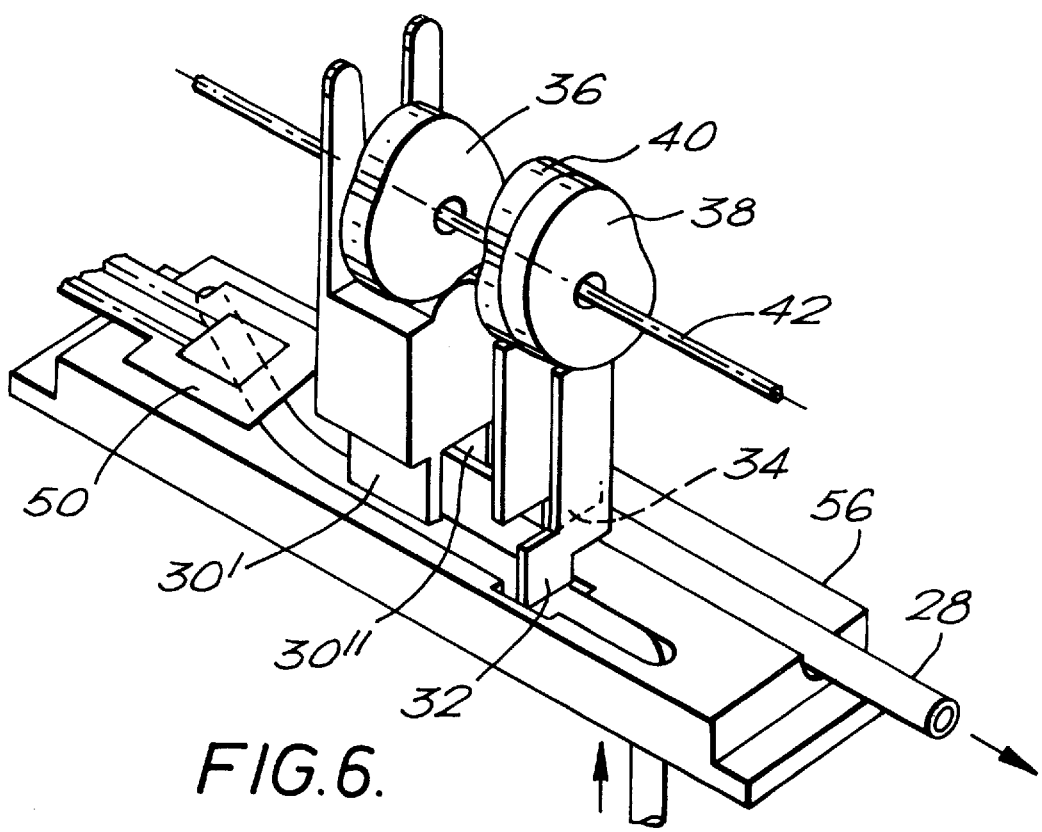
FIG. 6 shows the camming arrangement for operating the pushers and the valves.

Further specific details of the camming mechanisms are shown in FIG. 6. As will be seen, the line 28 is threaded into a series of grooves on a support plate 56. When the valves 32,34 move downwardly, the line 28 is crushed between the valves themselves and the support plate. Likewise, when the pushers 30', 30" move downwardly, the line 28 is at least partially compressed. In FIG. 6, the looped arrangement of the line 28 is not shown clearly: in fact, the line loops down below the support 56 immediately beyond the pressure plate 50.

Figure 7:
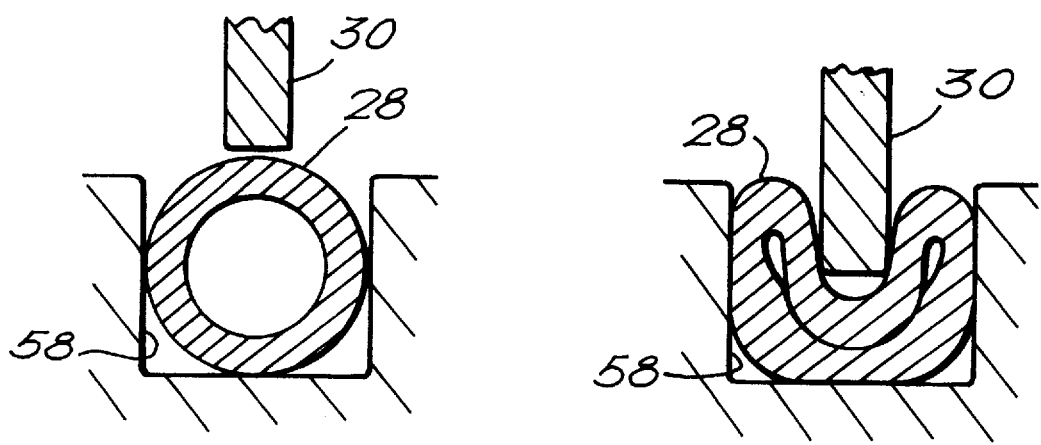
FIG. 7 shows how the tube is restrained within a channel as it is acted upon by the pushers.

The operation of the fingers 30', 30", are shown in more detail in FIG. 7. Where the line is compressed by the pushers, it is contained within a channel 58 within the plate 56. As the pusher moves downwardly, the line is partially compressed in on itself, as is shown in the right hand drawing.

The plate 56 (FIG. 6) may either be part of the removable cassette 22, or in a preferred embodiment it may be part of the main body 20 of the unit; in one example, the plate may be configured as a rotatable tube support on the main body 20, such as is described in co-pending application No PCT/GB94/02811.

The operation of the pump monitoring system will now be described with references to FIGS. 8 to 11, which illustrate the various pumping waveforms. The upper trace shows the voltage output of the pressure sensor 50, as a function of the angle of the camshaft 42. The second and third traces respectively show the positions of the output valve 34 and the input valve 32. Under that is shown the position of the pusher 30, and at the bottom are shown the signals provided by the opto-position sensor 54.

To achieve pump monitoring, the microprocessor 46 repeatedly checks the pressure sensor output during the pumping cycle. To ensure synchronisation, reference is made to the synchronisation pulses from the opto-position sensor 54. This novel method of monitoring the status of a peristaltic pump enables recognition of the following fault states: air in line, downstream occlusion (eg blocked cannula), upstream occlusion (eg empty bag), tubing incorrectly inserted, upstream over-pressure (eg patient squeezing bag), and disposable cassette not fitted.

Figure 8:
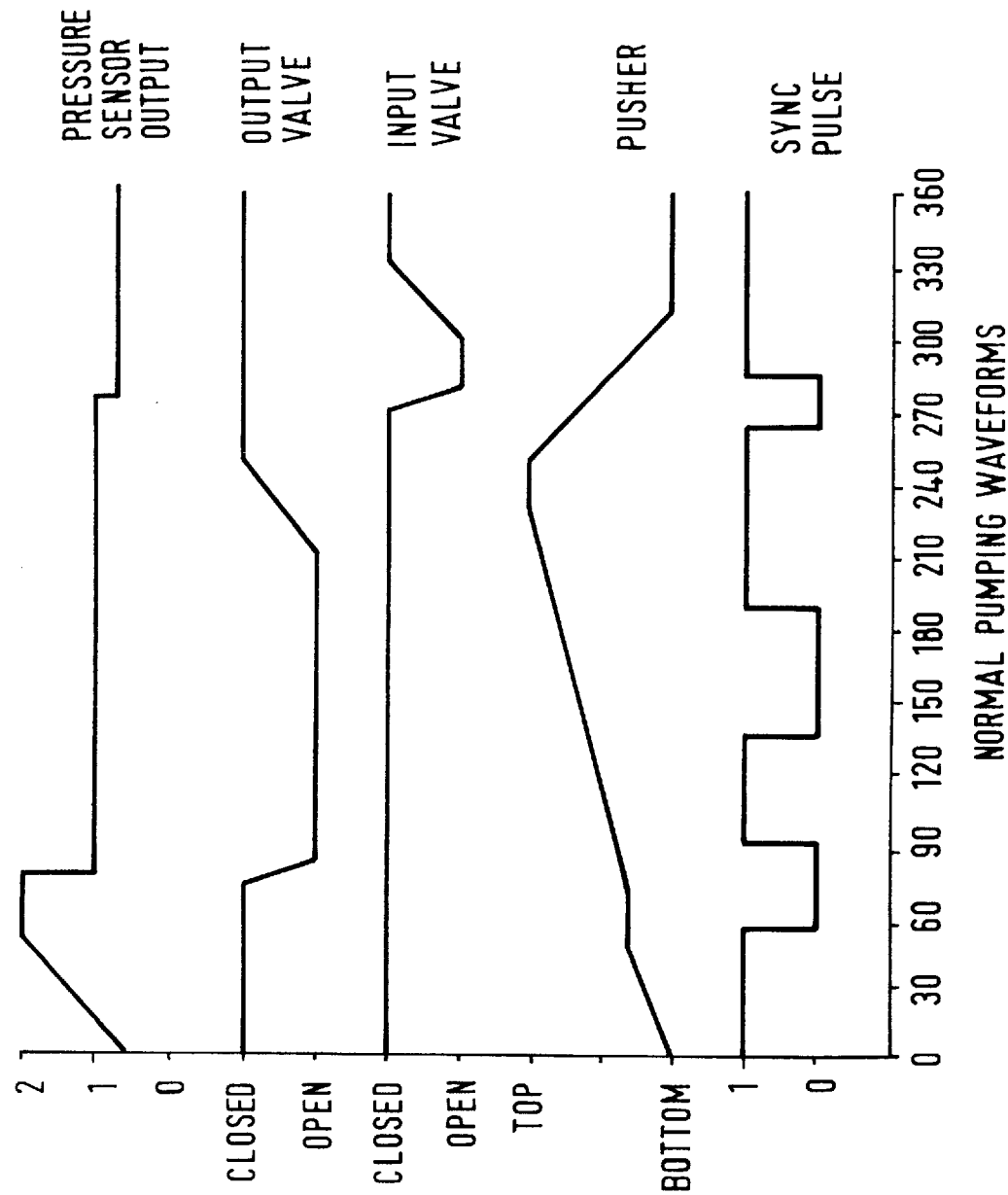
FIG. 8 shows the pumping waveforms in normal operation.

Referring first to FIG. 8, the waveforms are shown for normal operation, as a function of the camshaft angle. The major segments of the pump sequence are as follows:

0–45 degrees: With both valves shut, the pressure ramps up as the pusher progressively squashes the tubing.

45–70 degrees: The pusher pauses, the pressure stabilises at 400 mmHg (approx).

70–230 degrees: The output valve opens, permitting the pump chamber pressure to equalise with the downstream pressure; the pusher ramps to the top of its travel, expelling the fluid for this shot.

230–250 degrees: The outlet valve closes

265–310 degrees: The inlet valve opens and the pusher ramps downwards, withdrawing from tube.

310–340 degrees: Input valve closes.

340–360 degrees: Pump cycle is completed, motor stops.

The pressure sensor signal is significantly modified in the presence of the various fault conditions mentioned above.

Figure 9:
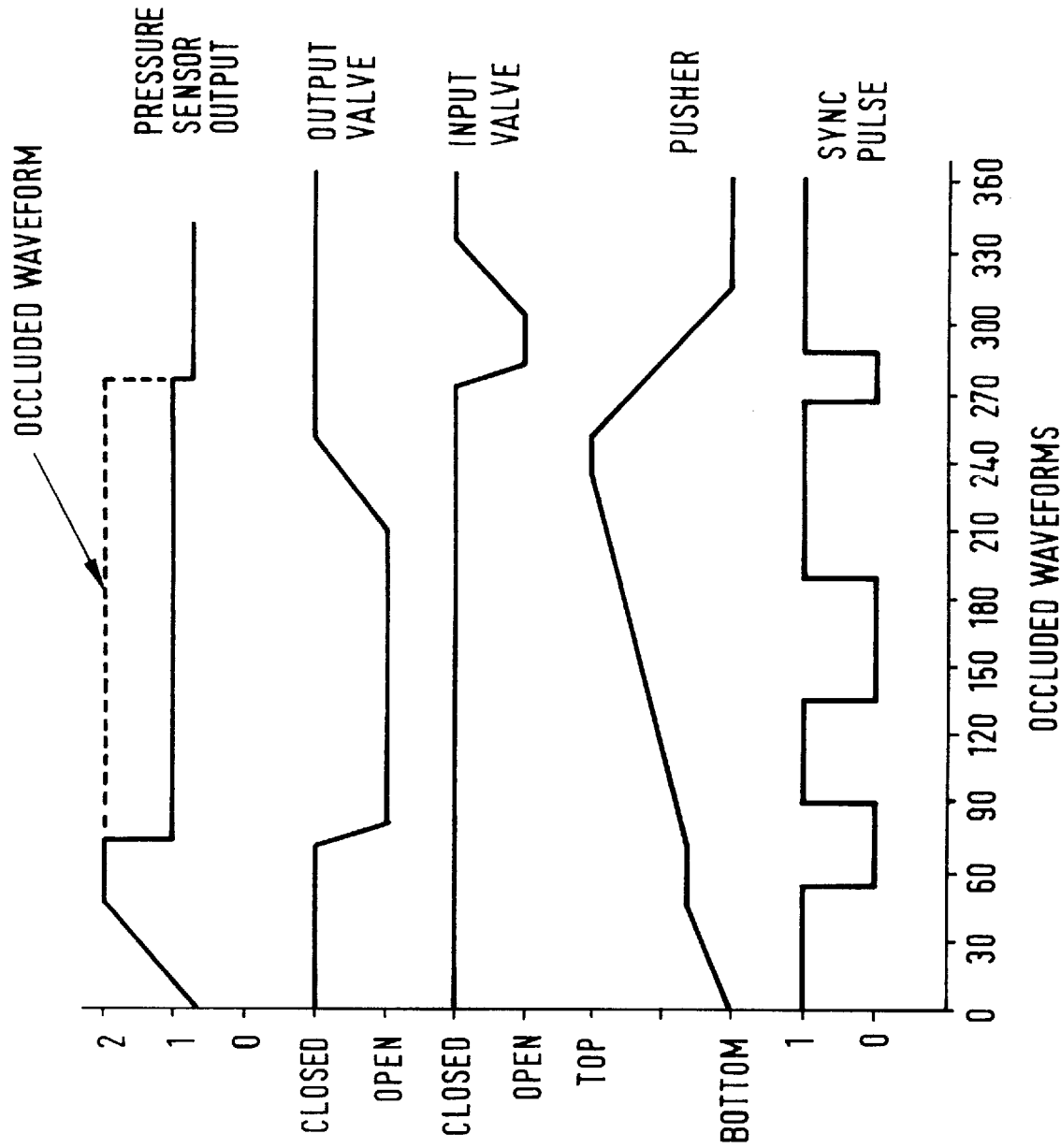
FIG. 9 shows the pumping waveforms when there is a downstream occlusion.

The dotted line of FIG. 9 shows what the pressure sensor output might look like if there is a downstream occlusion, for example if the cannula is blocked. As will be seen, the pressure sensor output remains high for camshaft angles between about 70 and 230 degrees. The occlusion pressure may be ascertained by comparing the output voltage (that is the pressure when the output valve is open and the input valve is closed) with the input voltage (that is the pressure when the output valve is closed and the input valve is open).

Figure 10:
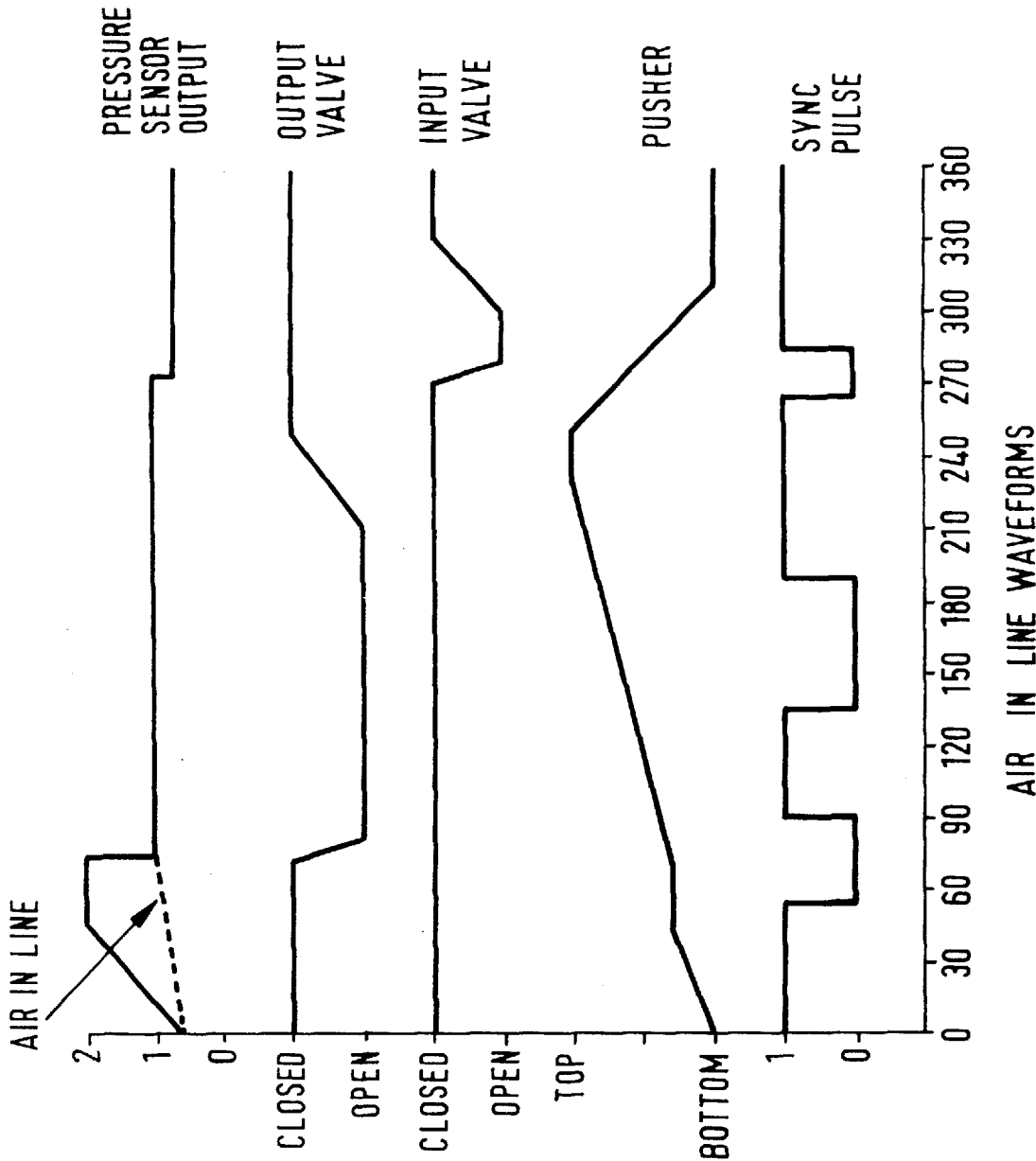
FIG. 10 shows the pumping waveforms when there is air in the line.

The dotted line in FIG. 10 shows how the pressure sensor output may vary if there is air in the line. When both of the valves are closed, and the pusher is moving downwardly (between 45 and 70 degrees) there is a positive pressure gradient. The amount of the gradient depends upon the amount of air in the central pump chamber, because air is much more easily compressed than the liquid infusate.

If it is known that the pressure is around atmospheric when the camshaft angle is zero degrees, then the pressure reached at 30 to 60 degrees may be used to indicate the amount of air in the central pump chamber. On the other hand, if it is known that the pressure is around atmospheric when the camshaft angle is 300 degrees, then the pressure reached at 45 to 70 degrees may be used to indicate the amount of air in the central pump chamber.

Figure 11:
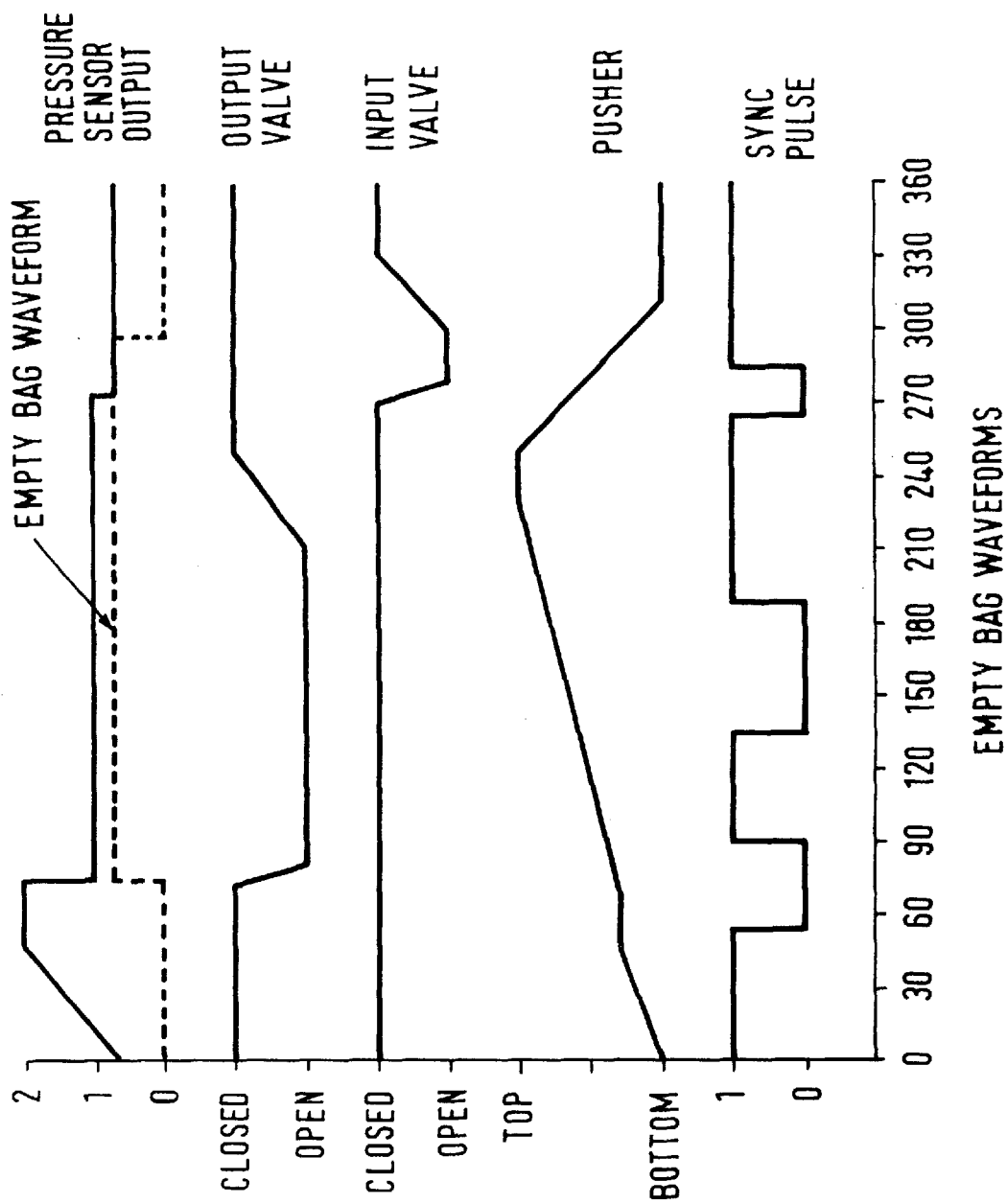
FIG. 11 shows the pumping wave forms when the bag is empty.

The dotted line in FIG. 11 shows a typical pressure sensor output in the event that the bag is empty. Normally, the input pressure will be substantially atmospheric. However, an upstream occlusion (such as an empty bag) can be detected by measuring the changes in input pressure from one cycle to the next. The algorithm is arranged to detect upstream occlusion if it finds three successive reducing values for the input pressure.

If the cassette is not fitted, the signal from the pressure sensor will be at zero volts permanently, regardless of the pump cycles.

It is not normally necessary to check for bag overpressure, in a portable device, since the flexible bag is normally protected by the rigid external cassette 22. In devices where the bag is accessible, however, it may be desirable to check for bag over-pressure, which would normally indicate that the bag is being squeezed. This would be done by comparing the input pressure with atmospheric pressure.

An exemplary fault-detection algorithm will now be set out, for use with a portable infusion unit such as is illustrated in FIG. 2.

Four parameters are derived from the pressure sensor waveform:

Vcomp—the voltage when the camshaft angle is 45–70 degrees.

Vip—the voltage corresponding to the inlet pressure.

Vop—the voltage corresponding to the outlet pressure.

Vref—voltage measured at start of cycle.

Also we define the following:

Vfaultmin: Minimum pressure sensor voltage for disposable cassette fitted.

Vocc: Required occlusion pressure threshold.

Vcompminus1: Vcomp for previous pump cycle.

Vipminus1: Vip for previous pump cycle.

Vair: Minimum compression pressure below which air alarm is given.

The algorithm then examines the pressure sensor waveform for possible fault conditions in the order shown below:

If Vref<=Vfaultmin THEN NO DISPOSABLE

If Vip>Vop+Vocc THEN DOWNSTREAM OCCLUSION

Vcompavg-(Vcomp+Vcompminus1)/2

Vipavg-(Vip+Vipminus1)/2

If (Vcompavg-Vipavg)<Vair THEN AIR IN LINE

If (Vip<Vipminus1-Vempty1) AND
(Vip<Vipminus2-Vempty2) AND
(Vip<Vipminus3-Vempty3) THEN
UPSTREAM OCCLUSION Finally, the variables are updated:

Vcompminus1=Vcomp

Vipminus3=Vipminus2

Vipminus2=Vipminus1

Vipminus1=Vip

Figure 12:
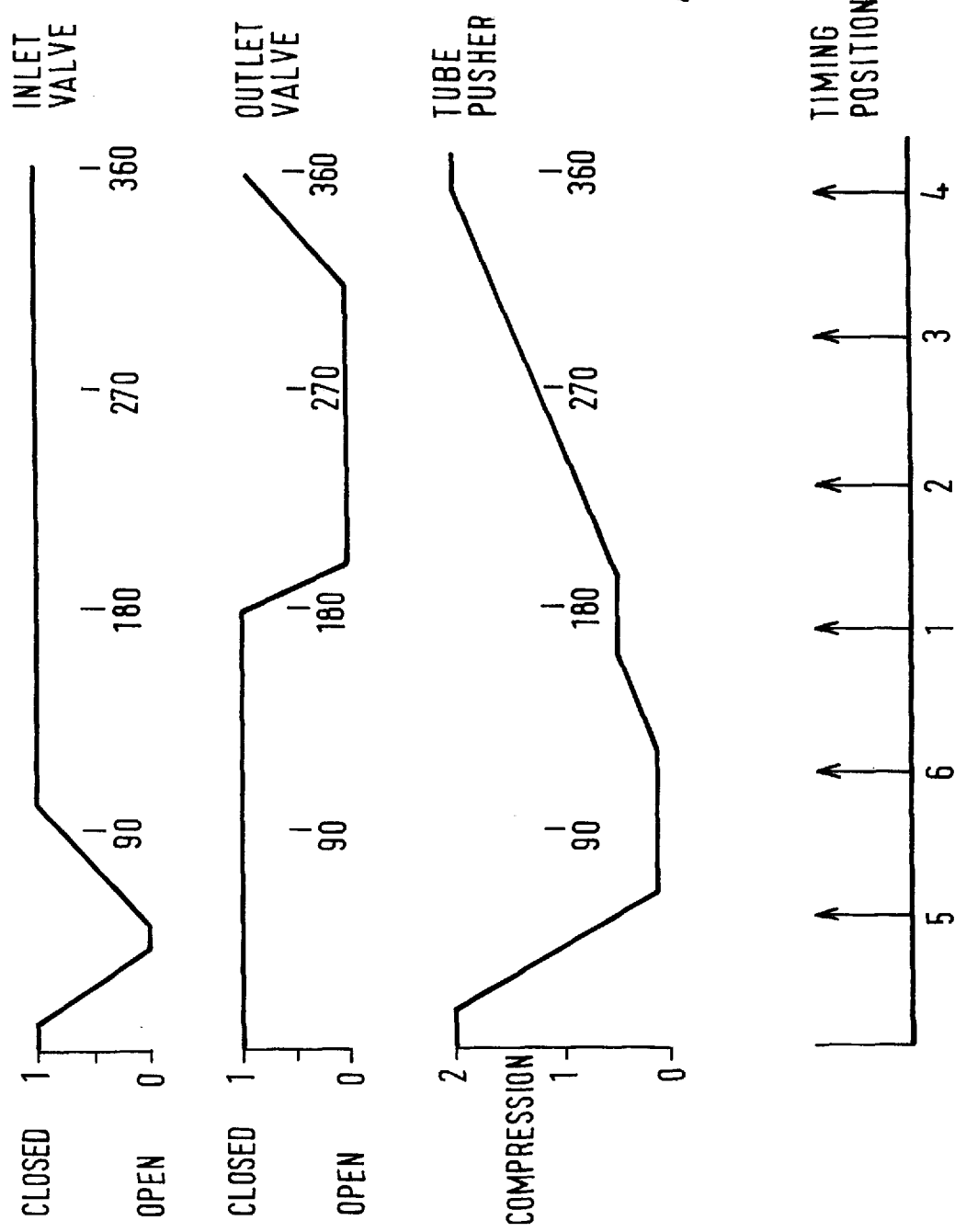
FIG. 12 shows the pumping waveforms of an alternative embodiment.

FIG. 12 shows some alternative waveforms representing a slight variation of the embodiments previous discussed. As before, the position of the inlet valve, the outlet valve and the tube pusher are shown as a function of the cam shaft angle. The bottom tracing of FIG. 12 shows the timing positions, that is the positions at which pressure readings are taken. These may be described as follows:

| 1 | Compression | Vcomp | Both valves closed, tube pusher + 0.4 mm |
| 2 | Outlet | Vop2 | Outlet valve opens, fluid output begins |
| 3 | Outlet | Vop3 | Middle of output |
| 4 | Outlet | Vop4 | End of outlet phase |
| 5 | Inlet | Vip | Outlet valve closes, inlet valve open |
| 6 | Rest Position | Vrest | Both valves closed, motor stopped |

The motor is stopped after the sixth reading, and then restarted again at the appropriate time to repeat the cycle.

Occlusion is detected by monitoring the two output signals Vop2, Vop4. The system computes a long term average that is used to produce a zero pressure reference. An occlusion alarm is given if the instantaneous value exceeds the average by an amount greater than a preset threshold.

The following algorithm shows how the average value is produced and the occlusion alarm signals produced—note that an occlusion alarm will be given if there is a rapid pressure rise in a single shot or the sensor voltage exceeds the maximum allowed.

We first define the following constants:

YOmm=Average value counter (2×Vatm)

Vatm=Assumed value for atmospheric pressure

The occlusion detecting algorithm is as follows:

```
IF Vop4 * 2 > YOmm THEN
    YOmm = YOmm+1
ELSE
    YOmm = YOmm-1
END
Vatm = YOmm / 2
IF (Vop4 - Vatm > OCCLUSIONLIMIT) THEN OCCLUSION
    OR (Vop4 - Vop2 > ( OCCLUSIONLIMIT * 2 /3)) THEN
                                        OCCLUSION
    OR (Vop2 > MAXALLOWED) THEN OCCLUSION
    OR (Vop4 > MAXALLOWED) THEN OCCLUSION
END
```

The air-in-line alarm relies on the pressure difference between the inlet and compression phases as described earlier. This is filtered to prevent a small volume of air from causing an alarm, as follows:

Vfilt=Vcomp-Vip

Yair=Vfilt+0.5 * Yair

The alarm is given on or after the 8th shot (i.e. 0.4 ml) after the start point if Yair is less than a set threshold Vair:

```
IF ShotCount >= 8 THEN AIR IN LINE
        IF Yair <= Vair THEN AIR IN LINE
        END
END
```

The cassette empty alarm works in a similar manner to the occlusion alarm, and uses an average value that is computed using a simple digital filtering algorithm. The alarm is given if the pressure drops below a preset limit, indicating suction. The filtering algorithm is as follows:

ZOmm=Vip+0.99 * ZOmm

Vinatm=Zomm/100

The alarm is given if:

Vinatm-Vip<BAGEMPTYLIMIT and

Vinatm−Vip$_{-1}$<BAGEMPTYLIMIT and
Vinatm−Vip$_{-2}$<BAGEMPTYLIMIT and
(That is the inlet pressure has to exceed the limit of −300 mmHg for 3 successive shots before the alarm is activated).

To produce the cassette removed alarm, a threshold is defined (Vnocassette) below which the cassette is regarded as have been removed—but to avoid a cassette empty condition from producing a false cassette removed alarm the following test is applied at the start position:

```
If FSR < Vnocassette OR
IF ShotCount >= 2 AND (Vop2 < Vnocassette)
    THEN CASSETTE REMOVED
END
```

Where FSR is the pressure value determined by the pressure sensing device.

FIGS. 13A to 13F show various stages in a pumping cycle of a pump constructed in accordance with a most preferred embodiment of the invention.

The pump incudes a motor and gearbox assembly 102 which drives cam assemblies 104,106,108 for the inlet valve 110, tube pusher 112 and outlet valve 114, respectively.

The tube 116, in this embodiment, is substantially straight between the inlet 110 and outlet 114 valves. The valves 110,114 and pusher 112 are all adapted to push on the tube 116 in substantially the same direction, against a pressure plate 118.

A FSR pressure sensor 120 is located between the inlet valve 110 and the pusher 112.

Figure 13A:
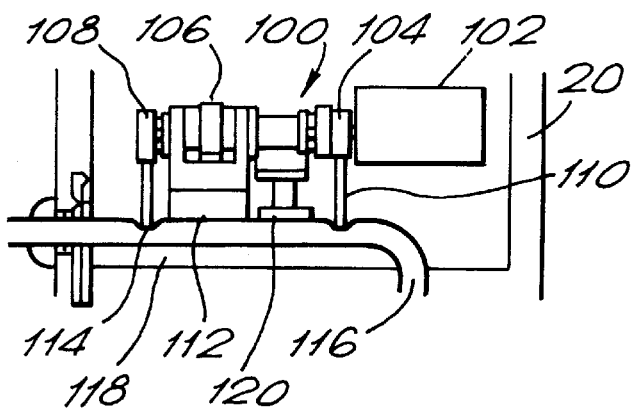
FIGS. 13A to 13F show various stages in a cycle of operation of a most preferred embodiment for the arrangement of a tube, pusher and valves.
Figure 13B:
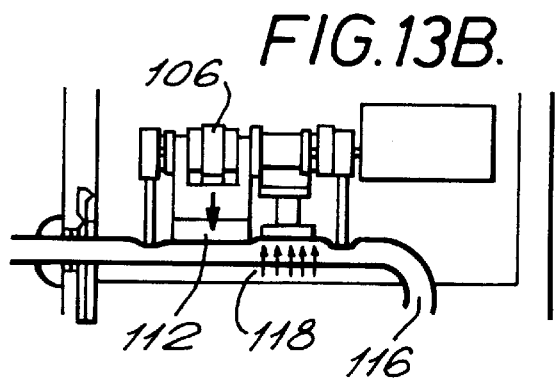
Figure 13C:
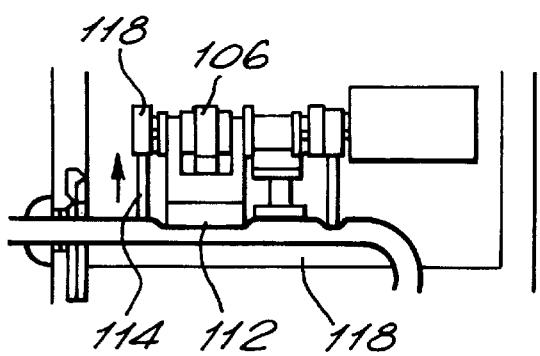
Figure 13D:
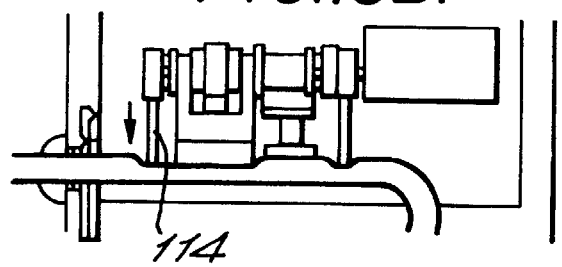
Figure 13E:
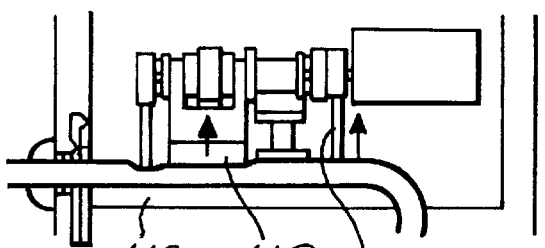
Figure 13F:
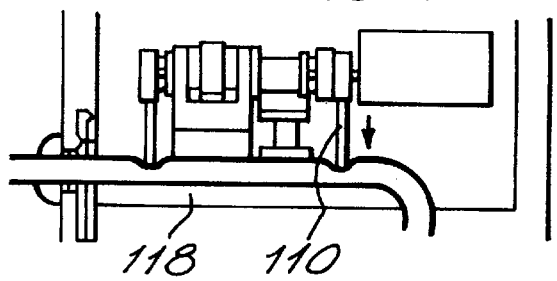

In FIG. 13A, the tube 116 is compressed by both of the inlet 110 and outlet 114 valves and the pusher 112 is retracted.

The arrangement of the cam assemblies 104,106,108 is such that the common shaft which they are located on rotates once during one pumping cycle. The cam assemblies are orientated so that the valves 110,114 and pusher 112 move sequentially through the configurations shown in FIG. 13A to FIG. 13F. Thus, as the cam assemblies 104,106,108 rotate from the FIG. 13A position to the FIG. 13B position, the pusher 112 is extended by its cam 106 towards the pressure plate 118 and the sensor 120 is capable of sensing increasing pressure in the tube 116. As the cam assemblies rotate from the FIG. 13B position to the FIG. 13C position, the outlet valve 114 is permitted to open by its cam assembly 118, permitting fluid in the tube 116 to flow out of the pump 100, as the pusher cam assembly 106 extends the pusher 112 fully towards the pressure plate 118. As the cam assemblies rotate from the position shown in FIG. 13C to the position shown in FIG. 13D, the outlet valve 114 closes again. Then, as the cam assemblies rotate from the FIG. 13D position to the FIG. 13E position, the inlet valve 110 and pusher 112 retract away from the pressure plate 118 to allow fluid to flow into the pump 100 from, for example, a cassette (not shown). As the cam assemblies rotate from the FIG. 13E position to the FIG. 13F position, the inlet valve 110 closes again, by extending towards the pressure plate 118. It will be noted that the valves 110,114 and pusher 112 have returned in FIG. 13F to the same positions shown in FIG. 13A.

The pump 100 has its cam assemblies 104,106,108 orientated to produce the wave forms shown in FIG. 12 and the monitoring of the pump is as described above with reference to FIG. 12. It will be appreciated that the pump 100 is incorporated in the body 20 of the infusion pump unit, as an alternative to the motor assembly, valves, pusher, and pressure sensor, described above with reference to FIGS. 4 to 6. The pressure plate 118 preferably incorporates a channel (not shown) similar to the channel 58 described above with reference to FIG. 7.

We claim:

1. A peristaltic pump comprising a flexible line carrying fluid to be pumped, cyclical line compression means arranged repeatedly to compress the line, the pump having an input valve upstream of the line compression means and an output valve downstream of the line compression means, pressure sensing means arranged to provide a signal representative of the pressure in the line between the input and output valves, the said signal being supplied to pump monitoring means, and the monitoring means having indicator means arranged to provide a pump status indication; characterised in that the pump monitoring means is arranged to monitor the compression pressure, when both the input and the output valves are closed and pressure is applied to the line by the line compression means.

2. A peristaltic pump as set out in claim 1 in which the monitoring means is arranged to monitor the input pressure, when the input valve is open and the output valve is closed.

3. A peristaltic pump as set out in claim 1 in which the monitoring means is arranged to monitor the output pressure, when the input valve is closed and the output valve is open.

4. A peristaltic pump as set out in claim 1 in which the pump monitoring means includes means for detecting whether a fluid supply is attached to the line.

5. A peristaltic pump as set out in claim 4 wherein the monitoring means is arranged to monitor the input pressure when the input valve is open and the output valve is closed, in which the means for detecting whether a fluid supply is attached to the line comprises means for determining whether the input pressure, or the mean input pressure, is higher than a reference value.

6. A peristaltic pump as set out in claim 1 in which the pump monitoring means includes means for detecting an occlusion downstream of the pump.

7. A peristaltic pump as set out in claim 6 wherein the monitoring means is arranged to monitor the output pressure when the input valve is closed and the output valve is open, in which the means for detecting an occlusion downstream of the pump comprises means for determining whether the output pressure, or the mean output pressure, is greater than a threshold value.

8. A peristaltic pump as set out in claim 1 in which the pump monitoring means includes means for detecting air in the line.

9. A peristaltic pump as set out in claim 8 in which the means for detecting air in the line comprises means for comparing the compression pressure with the input pressure, or for comparing the mean compression pressure with the mean input pressure.

10. A peristaltic pump as set out in claim 1 in which the pump monitoring means includes means for detecting an occlusion upstream of the pump.

11. A peristaltic pump as set out in claim 10 wherein the monitoring means is arranged to monitor the input pressure when the input valve is open and the output valve is closed, in which the means for detecting an occlusion upstream of the pump comprises means for detecting an input pressure decrease over several pump cycles.

12. A peristaltic pump as set out in claim 1 including a position sensor arranged to supply a synchronization signal to the pump monitoring means at each pump cycle.

13. A drug infusion unit incorporating a peristaltic pump comprising a flexible line carrying fluid to be pumped, cyclical line compression means arranged repeatedly to compress the line, the pump having an input valve upstream of the line compression means and an output valve downstream of the line compression means, pressure sensing means arranged to provide a signal representative of the pressure in the line between the input and output valves, the signal being supplied to pump monitoring means, and the monitoring means having indicator means arranged to provide a pump status indication; characterized in that the pump monitor means is arranged to monitor the compression pressure, when both the input and the output valves are closed and pressure is applied to the line by the line compression means.

14. A drug infusion unit as set out in claim 13 in which the peristaltic pump is contained within a main body of the unit, the main body being arranged to cooperate with a disposable cassette containing a bag within which is the drug to be infused, the bag including a flexible supply line on which the pump is arranged to operate when the cassette is in place.

15. A drug infusion pump as set out in claim 14 in which the supply line is bent through a loop of substantially 180°, with the input and output valves being adjacent to each other, one at each end of the loop, the compression means and the pressure sensing means being within the loop.

16. A drug infusion unit as set out in claim 15 in which there are two compression means within the loop, operating together to compress the line.

17. A drug infusion unit as set out in claim 16 in which the two compression means are adjacent to each other.

18. A drug infusion unit as set out in claim 13 in which the compression means, input valve, and output valve are all compression members, arranged to compress the line from the outside.

19. A drug infusion unit as set out in claim 18 in which the compression members compress the line against a fixed support which is part of the main body of the unit.

20. A drug infusion unit as set out in claim 18 in which the compression members operate by means of cams on a common camshaft.

21. A drug infusion unit as set out in claim 13 including a position sensor arranged to supply a synchronization signal to the pump monitoring means at each pump cycle.

22. A peristaltic pump including a flexible line carrying fluid to be pumped, line compression means arranged repeatedly to compress the line, an input valve upstream of the line compression means and an output valve downstream of the line compression means; the line compression means comprising a member which is arranged to compress the line against a support, the pump including restraining means preventing or restraining the line from bulging in a direction perpendicular to the compression direction.

23. A peristaltic pump as set out in claim 22 in which the member is an elongate plate, extending along the line, the thickness of the plate being less than the outer diameter of the line.

24. A peristaltic pump as set out in claim 21 in which the support defines a groove in which the line is located, the sides of the groove acting to prevent or restrain the line from bulging.

25. A peristaltic pump as set out in claim 24 in which the width of the groove is substantially equal to the outer diameter of the line.

26. A contamination-in-line detector comprising a line through which in use a fluid flows, pressure means arranged to apply pressure to the fluid within the line between an input valve and an output valve, and pressure sensing means arranged to provide a signal representative of the pressure in the line between the input and output valves, characterised in that the line is flexible and the pressure means applies pressure to the fluid within the flexible line by compressing said line, the pressure sensing means providing the signal when both the valves are closed and pressure is being applied by the pressure means.

27. A detector as claimed in claim 26 in which the pressure sensing means is also arranged to provide a signal representative of the pressure in the line when either or both of the valves are open, or when both of the valves are closed but no pressure is being applied by the pressure means.

28. A detector as claimed in claim 26 in which comparison means is provided to compare the two pressures and thereby provide a determination of whether there is contamination in the line.

29. A detector as claimed in claim 26 in which calculation means is provided to produce an estimate of the amount of contamination.

* * * * *

UNITED STATES PATENT AND TRADEMARK OFFICE
CERTIFICATE OF CORRECTION

PATENT NO.   : 5,807,322
DATED        : September 15, 1998
INVENTORS    : Michael J. Lindsey et al.

It is certified that error appears in the above-identified patent and that said Letters Patent is hereby corrected as shown below:

Inventors: "Michael J. Lindsey, Berkhampsted" should be --Michael J. Lindsey, Hertfordshire--.

Column 10, claim 1, line 11;
   Delete "said".

Column 12, claim 24, line 12;
   "Claim 21" should be --Claim 22--.

Signed and Sealed this

Twenty-third Day of March, 1999

*Attest:*

Q. TODD DICKINSON

*Attesting Officer*          *Acting Commissioner of Patents and Trademarks*